United States Patent [19]

Burch

[11] Patent Number: 4,739,025

[45] Date of Patent: Apr. 19, 1988

[54] RADIATION RESISTANT POLYPROPYLENE-CONTAINING PRODUCTS

[75] Inventor: George N. B. Burch, Covington, Ga.

[73] Assignee: Hercules Incorporated, Wilmington, Del.

[21] Appl. No.: 859,298

[22] Filed: May 5, 1986

[51] Int. Cl.$^4$ ............................................. B29C 47/88
[52] U.S. Cl. ...................... 526/348.1; 264/176.1; 264/211.14; 264/211.22; 264/211.24; 264/178 F; 264/210.2; 264/210.3; 264/210.8; 523/136; 526/351; 526/936
[58] Field of Search ........... 264/176.1, 211.14, 211.22, 264/211.24, 178 F, 103, 210.2, 210.3, 210.8; 425/66, 71; 522/10, 78, 912; 523/136; 526/348.1, 351, 936

[56] References Cited

U.S. PATENT DOCUMENTS

| | | | |
|---|---|---|---|
| 3,059,991 | 10/1962 | Munt | 425/66 |
| 3,079,312 | 2/1963 | Alsys | 204/154 |
| 3,143,523 | 8/1964 | Caldo | 264/235.6 |
| 3,152,380 | 10/1964 | Martin | 264/235 |
| 3,165,563 | 1/1965 | Rasmussen | 264/22 |
| 3,215,486 | 11/1965 | Hada et al. | 264/210.3 |
| 3,345,447 | 10/1967 | Grant | 264/235 |
| 3,383,375 | 5/1968 | van der Vegt et al. | 264/235 |
| 3,500,626 | 3/1970 | Sandiford | 264/210.8 |
| 3,530,108 | 9/1970 | Oppenlander | 264/210.8 |
| 3,621,088 | 11/1971 | Hatcher et al. | 264/210.8 |
| 3,946,094 | 3/1976 | Kanetsuna et al. | 264/178 F |
| 4,110,185 | 8/1978 | Williams et al. | 204/159 |
| 4,274,932 | 6/1981 | Williams et al. | 204/159 |
| 4,460,445 | 7/1984 | Rekers | 204/159 |
| 4,467,065 | 8/1984 | Williams et al. | 524/296 |
| 4,551,296 | 11/1985 | Kavesh et al. | 264/177 |

FOREIGN PATENT DOCUMENTS 0078603 9/1982 European Pat. Off. .
1050802 12/1966 United Kingdom .

OTHER PUBLICATIONS

European Polymer Journal, 15, 379–387 (1979).
ACS Symposium Series No. 280, pp. 359–371 (1985), Carlson, Dobbin, Jensen and Wiles.

*Primary Examiner*—Jeffery Thurlow
*Attorney, Agent, or Firm*—John E. Crowe

[57] ABSTRACT

A product and method for obtaining a radiation-resistant polyolefin-containing product, by handling and processing the corresponding homopolymer or copolymer melt and resulting extrudate in a manner favoring retention of a high smectic and less than about 20 wt % monoclinic configuration.

11 Claims, No Drawings

RADIATION RESISTANT POLYPROPYLENE-CONTAINING PRODUCTS

The instant invention relates to a method for obtaining radiation-resistant polyolefin-containing articles and materials, and the corresponding articles and materials obtained thereby.

BACKGROUND

Medical or medically-oriented products constitute a large market for various polymeric materials, including nonwoven fabrics, as well as extrudable polymeric syringes, tubing, tissue culture flasks, packaging films, and the like.

At present, this market is generally dominated by latex-bonded polyesters and rayons, with polypropylene homopolymers and copolymers occupying a marginal role at best. This is due, to a great extent, to the need to expose such polymeric material to sterilizing doses of radiation, particularly gamma radiation in order to conveniently satisfy hygienic guidelines. A number of polymers, particularly polyolefin homopolymers and copolymers, however, are severely degraded or damaged by radiation exposure, causing unpleasant odor, discoloration, brittleness, and general loss of strength.

A number of additives such as hydrocarbon oils, halogenated hydrocarbon oils, phthalic acid esters, vegetable oils, silicon oils (Ref. U.S. Pat. Nos. 4,110,185, 4,274,932, 4,467,065), various organic carboxylic acids and organic phosphites (British Pat. No. 1,050,802), hindered phenol, and benzaldehyde stabilizers (U.S. Pat. No. 4,460,445) have been proposed and used in the art, with varying degrees of success, to minimize one or more of the above problems. None of such additives, however, capable of satisfactorily controlling long range damage due to sterilizing amounts of gamma radiation, particularly those products comprising fibers and/or films containing substantial amounts of polyolefin.

It is an object of the present invention to develop a method for obtaining radiation resistant polyolefin-containing products.

It is a further object of the present invention to increase resistance to gamma radiation-induced damage to polypropylene-containing fiber and film extrusion products.

THE INVENTION

The above objects are obtained, in accordance with the present invention, by utilizing the steps of (a) extruding degraded polyolefin-containing polymeric melt having a narrow molecular weight ($\overline{Mw}/\overline{Mn}$) distribution through a die or spinnerette under temperature and take up conditions to obtain an extrudate high in smectic phase with a monoclinic crystalline phase of less than about 20 wt%, and thereafter (b) altering dimensions of the extrudate to obtain a product under temperature and working conditions favoring minimal increase in the monoclinic crystalline phase.

For purposes of the present invention, the term "radiation-resistant" is conveniently defined as a filament, fiber or film showing a substantially reduced amount of brittleness or strength loss (i.e. aging) upon exposure to a sterilizing amount of gamma radiation.

For test purposes, gamma radiation damage is conveniently measured by standard tests directed to Elongation Retention and Tenacity Retention properties.

The term "polyolefin-containing", as used herein, is usefully a polymeric composition containing about 5-100 wt% and preferably 15 wt%-100 wt% of polyolefin homopolymer, particularly polypropylene or corresponding copolymer such as propylene/ethylene and the like. Generally speaking, such material has a weight average molecular weight of about $3 \times 10^5$ through $10 \times 10^5$ and preferably falls within a range of about $5-9 \times 10^5$.

For purposes of the present invention the term "extrudate" is conveniently defined as a filament, fiber yarn, fiber web or film which is initially taken up at a stretch ratio not exceeding about 1:1.30 unless (1) the take up involves filament, fiber yarn, or film which is initially and consistently maintained above the melt crystallization temperature, or
(2) the take up involves filament, fiber yarn, or film of high smectic and low monoclinic configuration which is already at ambient temperature.

For obtaining the low monoclinic and high smectic crystal phases in accordance with the present invention it is important that the molecular weight of the polymer be sufficiently high to permit degradation by peroxide or similar art-known means to obtain a relatively narrow molecular weight distribution ($\overline{Mw}/\overline{Mn}$ of about 3–6) within the spin melt. If lower molecular weights are employed, strict control over stress and temperature at the threadline becomes increasingly important.

If desired, polyolefin-containing material for present purposes may include linear polyethylene and, as desired, linear polyolefin material, alone or in combination with about 1 wt%-20 wt% of a corresponding branched polyolefin material possessing melt indices within a range of about 1-50.

The term "product", as used herein, includes fiber having a denier range of about 1-15 dpf in which the ratio of initial extrusion dimensions-to-final dimension does not exceed a stretch orientation ratio exceeding about 1:1.50 and preferably does not exceed about 1:1.10 unless subsequent take up and stretching steps are continuously carried out under strict temperature control, as above described, and subsequent working and stretching conditions favor a minimal increase in the monoclinic crystalline phase.

The term "high" as associated herein with the term "smectic phase" is usefully defined as a smectic crystalline phase of not less than 40 wt%-75 wt% as measured by the general relationship established between SAXS-L values of a spun or initially extruded material and the elongation retention values arrived at after drawing or working, the relation being generally spelled out in Table II.

Based on this relationship it is found (1) that sensitivity to radiation tends to increase in linear proportion to monoclinic content as measured by the x-ray defraction values and (2) that by comparison of wide angle and small angle x-ray data it is found that SAXS-L values are a convenient way of measuring the relative amount of smecticity of the final polymeric product.

In any case, the fiber- or film-working steps should favor a product having about 20 wt% of monoclinic crystalline phase or less, and a smectic phase of about 40 wt%-75 wt%.

Retention of the desired crystal/orientation conditions, above described, is further aided by incorporating up to about 8 wt% of ethylene/propylene copolymer in the melt, as noted above, although the instant invention is not limited to such inclusion.

In accordance with the above findings, it has also been found that low denier (1–5 dpf) polyolefin-containing fiber and thin film extrudates are substantially more sensitive to polymeric changes favoring increased orientation (i.e. increased monoclinic crystalline state) than are fibers and films of a thicker range (i.e. 6–20 dpf or higher).

Polymer melts within the present invention can also usefully include various art-recognized additives, provided such additives do not substantially provoke or favor fiber or film orientation, and the formation of substantially greater than 20 wt% of a monoclinic crystalline phase.

Such additives for use within the present invention can include, for instance, pH stabilizers such as calcium stearate, antioxidants, degrading agents, pigments, including art-known whiteners and colorants such as $TiO_2$ and the like. Generally such additives are incorporated in art-recognized concentrations varying normally from about 0.1%–3% by weight of spin melt.

A "sterilizing amount of radiation", for present purposes, usefully comprises exposure to about 2–10 Mrad or higher, of gamma radiation, and preferably about 2–6 Mrad from a Cobalt 60 or equivalent source.

For test purposes, radiation degredation resistance is most conveniently measured, as noted above, in terms of elongation retention and tenacity retention.

The present invention is further illustrated, but not limited by the following examples:

EXAMPLE I

Test polypropylene yarns are prepared having (a) a high smectic and (b) an essentially low monoclinic crystalline phase for comparison testing of gamma radiation-resistant properties, based on fiber elongation retention and fiber tenacity retention; for such purpose, a smectic morphology and low monoclinic concentration is conveniently identified and generally assured by an SAXS-L[*1] value of less than about 120 Å for spun or initially extruded products.

*1. Long spacing of crystallinity determined by small angle x-ray spectroscopy.

A. A stabilizing mixture comprising antioxidant, [*2] hindered amine, [*3] calcium sterate, and a prodegradant, [*4] in respective 0.1% amounts, is blended into degraded polypropylene flake having a weight average molecular weight of $3.1 \times 10^{5[*5]}$ and melt spun at 235° C. and 2000 meters per minute take up, to obtain yarn of 4.7 denier having a melt flow rate of 20 and an SAXS-L of 144 Å. The spun yarn, hereafter identified as T-1A and TC-1A (control), is drawn at a rate of 200% extension per minute.

*2. Obtainable commercially from American Cyanamid under the trademark Cyanox ® 1790.
*3. Obtainable from Ciba Geigy as Chimassorb ® 944.
*4. Obtainable commercially from Penwalt Corporation under the trademark Lupersol ® 101.
*5. Available commercially from Himont Inc. as PRO-FAX ® 6301.

B. The stabilizing mixture of Example I A. is blended into a separate polypropylene flake having a weight average molecular weight of $9.1 \times 10^{5[*6]}$, and spun at 305° C.[*7] at 600 meter per minute take up, to obtain a yarn of 5.9 denier having a melt flow rate of 35 and SAXS-L of 110 Å. The spun yarn identified as T-2B and TC-2B (control), is drawn at a rate of 200% extension per minute as in (A) supra.

*6. Available commercially from Himont Inc. as PRO-FAX ® 6801.
*7. Using a standard 210 hole spinnerette.

C. The T-1 and T-2 test yarns of Examples I A. and I B. are exposed respectively to 2.5 and 5.0 Mrads of gamma radiation and stored together with their respective unradiated controls for 28 days at 60° C. before testing for elongation and tenacity retention.

Test results and evaluation are reported in Table I below.

TABLE I

| Sample # | Denier | Draw | Exposure (Mrad) | Elongation Retention | Tenacity |
|---|---|---|---|---|---|
| T-1A | 4.7 | 1.06 | 2.5 | 62 | 70 |
| T-1A | 4.7 | 1.06 | 5.0 | 19 | 68 |
| TC-1A | 4.7 | 1.06 | — | NC | NC |
| T-1A | 4.7 | 1.10 | 2.5 | 60 | 75 |
| T-1A | 4.7 | 1.10 | 5.0 | 17 | 71 |
| TC-1A | 4.7 | 1.10 | — | NC | NC |
| T-1A | 4.7 | 1.82 | 2.5 | 45 | 75 |
| T-1A | 4.7 | 1.82 | 5.0 | 27 | 53 |
| TC-1A | 4.7 | 1.82 | — | NC | NC |
| T-2B | 5.9 | 1.30 | 2.5 | 100 | 86 |
| T-2B | 5.9 | 1.30 | 5.0 | 98 | 73 |
| TC-2B | 5.9 | 1.30 | — | NC | NC |
| T-2B | 5.9 | 1.67 | 2.5 | 97 | 83 |
| T-2B | 5.9 | 1.67 | 5.0 | 100 | 73 |
| TC-2B | 5.9 | 1.67 | — | NC | NC |
| T-2B | 5.9 | 2.36 | 2.5 | 91 | 71 |
| T-2B | 5.9 | 2.36 | 5.0 | 81 | 56 |
| TC-2B | 5.9 | 2.36 | — | NC | NC |

EXAMPLE II

Profax 6801, in flake form, and having a weight average molecular weight of about $9.1 \times 10^5$ is blended and extruded with the stabilizing mixture of Example I except for the use of 0.06% (rather than 0.1%) of Cyanox 1790, and thereafter spun using the 210 hole spinerette of Example I at 275° C., to obtain test yarns of 2.8 and 8.5 dpf respectively.

The final drawn yarns, identified as T-3 through T-9, are obtained using a feed roll and a draw roll (300 M/min at 115° C.). Multiple yarn samples are then irradiated and stored as before for 28 days at 60° C. and thereafter tested for elongation retention. Test results are reported in Table III.

In line with earlier-stated evaluation of smectic and monoclinic phases based on SAXS-L values, a perceived correlation between Elongation Retention values (i.e. Drawn) and SAXS-L values of the corresponding Spun Yarn (not drawn) is set out in Table II below.

TABLE II

| Drawn Yarn % Elongation Retention | Spun Yarn SAXS-L Values Å |
|---|---|
| 95 | 107.5 |
| 85 | 110.0 |
| 67.5 | 115.0 |
| 48.0 | 120.0 |
| 30.0 | 125.0 |
| 12.0 | 130.0 |

TABLE II-continued

| Sample # | Polymer Profax | Final Denier | SAXS-L Å Spun Yarn | Drawn Yarn Tenacity g/d | Elong % | Elongation Retention[14] 3.24 Mrads | 5.36 Mrads |
|---|---|---|---|---|---|---|---|
| T3 | 6801 | 5.41[9] | 128.4 | 3.07 | 157 | 16% | 15% |
| T4 | 6801 | 5.43[9] | 112.5 | 1.67 | 373 | 82% | 82% |
| T5 | 6301 | 5.44[10] | 115.1 | 1.78 | 397 | 79% | 65% |
| T6 | 6501 | 2.06[11] | 128.6 | 2.62 | 136 | 18% | 14% |
| T7 | 6801 | 1.83[12] | 113.6 | 3.34 | 125 | 81% | 23% |
| T8 | 6801 | 1.86[13] | 106.4 | 3.22 | 129 | 85% | 55% |
| T9 | 6801 | 1.89[13] | 122.2 | 3.36 | 116 | 32% | 19% |

[9] 8.5 dpf Spun Yarn; MW $9.1 \times 10^5$; MFR 3.9 and 30.6 respectively.
[10] 8.5 dpf Spun Yarn; MW $3.1 \times 10^5$; MFR 31.0.
[11] 2.8 dpf Spun Yarn; MW $5.0 \times 10^5$; MFR 19.5.
[12] Same as T4 but 2.8 dpf and MFR 26.5.
[13] 1.9 dpf Spun Yarn; MW $9.1 \times 10^5$; MFR 22.8 and 16.4.
[14] See Table II.

What I claim and desire to protect by Letters Patent is:

1. A method for obtaining a radiation-resistant polyolefin-containing product, comprising
   (a) extruding degraded polyolefin-containing melt having a narrow molecular weight distribution to obtain an extrudate high in smectic phase, with a monoclinic crystalline phase of less than about 20 wt%; and thereafter
   (b) altering the dimensions of said extrudate to obtain a product under temperature and working conditions favoring minimal increase in said monoclinic crystalline phase.

2. The method of claim 1 wherein the extrudate comprises about 40-75 wt% of smectic crystalline phase.

3. The method of claim 1 wherein the polyolefin-containing melt comprises about 5-100 wt% of a polyolefin homopolymer or copolymer.

4. The method of claim 3 in which the polymeric melt comprises polypropylene homopolymer or copolymer having a weight average molecular weight within the range of about $3 \times 10^5 - 10 \times 10^5$.

5. The method of claim 4 in which the polymeric melt comprises a polypropylene homopolymer or copolymer having a weight average molecular weight within the range of about $5-9 \times 10^5$.

6. The method of claim 1 wherein the extrudate is used to form a woven or nonwoven material comprising polypropylene fiber of homogeneous or mixed denier.

7. The method of claim 1 wherein the extrudate is a a film.

8. The method of claim 1 wherein the extrudate is a fibrillated film.

9. The method of claim 1 wherein the polyolefin-containing melt contains an active amount of at least one antioxidant.

10. The method of claim 1 wherein the polyolefin-containing melt contains a hindered amine.

11. A radiation-resistant product obtained in accordance with claim 1 and consisting essentially of at least one of fiber or film extrudate obtained from a polyolefin-containing polymeric melt having a weight average molecular weight of about $3 \times 10^5 - 10 \times 10^5$, and a smectic crystalline phase of not less than 40 wt.%-75 wt.% as measured by SAXS-L values.

* * * * *

UNITED STATES PATENT AND TRADEMARK OFFICE
CERTIFICATE OF CORRECTION

PATENT NO. : 4,739,025
DATED : April 19, 1988
INVENTOR(S) : George N. B. Burch

It is certified that error appears in the above-identified patent and that said Letters Patent are hereby corrected as shown below:

Column 4, line 37 of Table 1 the following was omitted

"NC = No Change"

Signed and Sealed this

Twenty-third Day of August, 1988

Attest:

DONALD J. QUIGG

Attesting Officer

Commissioner of Patents and Trademarks